United States Patent

Thigpen

[11] Patent Number: 5,876,570
[45] Date of Patent: *Mar. 2, 1999

[54] PURIFICATION PROCESS FOR CYCLIC FORMALS

[75] Inventor: Hubert H. Thigpen, Corpus Christi, Tex.

[73] Assignee: Hoechst Celanese Corporation, Somerville, N.J.

[*] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,690,793.

[21] Appl. No.: 612,599

[22] Filed: Jan. 18, 1996

Related U.S. Application Data

[63] Continuation of Ser. No. 179,846, Jan. 11, 1994, abandoned.

[51] Int. Cl.[6] .......................... B01D 3/34; C07D 317/12
[52] U.S. Cl. ................. 203/63; 203/64; 549/430
[58] Field of Search .................. 203/14, 63, 17, 203/64, 71; 549/430; 568/601

[56] References Cited

U.S. PATENT DOCUMENTS

| | | | |
|---|---|---|---|
| 2,350,940 | 6/1944 | Squires | 260/338 |
| 4,007,095 | 2/1977 | Wolf et al. | 203/64 |
| 4,254,246 | 3/1981 | Dicoi et al. | 203/71 |
| 4,801,358 | 1/1989 | Berg et al. | 203/64 |
| 4,806,209 | 2/1989 | Berg et al. | 203/64 |
| 5,254,744 | 10/1993 | Neumer | 568/601 |

*Primary Examiner*—Virginia Manoharan
*Attorney, Agent, or Firm*—James M. Hunter, Jr.

[57] ABSTRACT

A purification process for cyclic formals, in which water is efficiently removed from a crude cyclic formal, namely, a mixture of a cyclic formal and water which is difficult to be separated from the mixture, thereby obtaining a cyclic formal of high purity which contains only a very small amount of water.

The purification process for cyclic formals is characterized by the steps of supplying a mixture of a cyclic formal and water into a distillation tower, effecting distillation while supplying a hydrophilic solvent (A) having a boiling point from 180° to 250° C. into the distillation tower at a position higher than the supply position of the mixture, and taking out a purified cyclic formal as a distillate.

10 Claims, 2 Drawing Sheets

PURIFICATION PROCESS FOR CYCLIC FORMALS

This application is a continuation application of U.S. Ser. No. 08/179,846 filed on Jan. 11, 1994, now abandoned.

BACKGROUND OF THE INVENTION

1. Field of the Invention:

The present invention relates to a purification process for cyclic formals which are useful as solvents, intermediates of drugs, starting materials for resins, and the like. More particularly, it relates to an economically advantageous purification process for obtaining cyclic formals of high purity which contains only a very small amount of water, in which water is efficiently removed from a mixture of a cyclic formal and water which is difficult to be separated from the mixture because of the azeotropy between cyclic formal and water.

2. Description of Related Art:

Cyclic formals typified by 1,3-dioxolan, 1,4-butanediol formal, diethylene glycol formal, 4-methyl-1,3-dioxolan, 1,3-dioxane, 1,3,6-trioxolane, etc. are known to be obtainable from cyclizing reactions between a corresponding glycol and an aldehyde, and between a corresponding alkylene oxide and an aldehyde. For example, concerning a method for preparing a typical cyclic formal, 1,3-dioxolan, German patent No. 1914209 discloses a process for preparing it by reacting glycol with formaldehyde in the presence of an acid catalyst, and Ind. Eng. Chem., 46,787 (1954) and U.S. Pat. No. 3,857,759 both disclose a process for preparing 1,3-dioxolan by reacting glycol and paraformaldehyde in the presence of an acid catalyst.

These processes for preparing cyclic formals which employ a glycol and an aldehyde as starting materials involve drawbacks in that the cyclic formal produced and a by-produced water or water which is present in a form of an aqueous aldehyde solution often co-boil (azeotropy), thereby rendering separation of water difficult by ordinary distillation steps.

Taking 1,3-dioxolan as an example, the above mentioned German patent No. 1914209 describes that as much as 7% of water is contained. In order to obtain 1,3-dioxolan of high purity by removing water from a mixture of 1,3-dioxolan and water, the above-mentioned Ind. Eng. Chem., 46,787 (1954) discloses a process in which a reaction distillate containing 1,3-dioxolan and water is added with sodium chloride for phase separation into two phases, and the organic phase is subjected to a purifying distillation for purification, while U.S. Pat. No. 3,857,759 discloses a process in which a reaction distillate is added with cyclohexane before purification. However, the former is not suitable as an industrial purification process, and the latter raises a problem in that water cannot be separated sufficiently for obtaining 1,3-dioxolan of high purity.

These phenomena do not specifically occur only in processes for preparing 1,3-dioxolan, but are common in processes for obtaining cyclic formals which form an azeotropic system with water. Accordingly, an economical purification process for obtaining cyclic formals of high purity in which water is efficiently removed from a mixture of a cyclic formal and water has still been desired.

Under the above circumstances, the present inventors have carried out extensive studies in order to solve the aforementioned problems. Having started from the use of extraction distillation, they have conducted researches focusing on solvents to be used, leading to completion of the present invention.

SUMMARY OF THE INVENTION

Accordingly, an object of the present invention is to provide a purification process for a cyclic formal which comprises the steps of supplying a mixture of a cyclic formal and water into a distillation tower at a supply position, effecting distillation while supplying a hydrophilic solvent (A) having a boiling point from 180° to 250° C. into the distillation tower at a position higher than the supply position of the mixture, and taking out a purified cyclic formal as a distillate from the top of the tower.

Another object of the present invention is to provide a purification process for a cyclic formal as described above, wherein the hydrophilic solvent (A) is a polyol, a dimer thereof, or a monoalkylether of a polyol or the dimer.

Another object of the present invention is to provide a purification process for a cyclic formal as described above, wherein the hydrophilic solvent (A) is selected from the group consisting of 1,4-butanediol, diethylene glycol, 1,2-propanediol, 1,3-propanediol, dipropylene glycol and monoalkyl ethers thereof.

Another object of the invention is to provide a purification process for a cyclic formal as described above, wherein the quantity of the hydrophilic solvent (A) supplied is from 1 to 15 times, on a molar basis, the quantity of water in the mixture of cyclic formal and water.

Another object of the invention is to provide a purification process for a cyclic formal as described above, wherein the distillation tower is a plate distillation tower, and the position at which the hydrophilic solvent (A) is supplied is the position of the second or any lower plate counted from the top plate.

Another object of the invention is to provide a purification process for a cyclic formal as described above, wherein the distillation tower is a packed distillation tower, and the position at which the hydrophilic solvent (A) is supplied is the position of a theoretical plate having a number not less than 0.5 counted from the top plate of the packed distillation tower.

Another object of the invention is to provide a purification process for a cyclic formal as described above, wherein a pre-concentrated mixture which contains a cyclic formal having a concentration more than 80% by weight up to a concentration which forms an azeotrope is supplied to the tower.

Another object of the invention is to provide a purification process for a cyclic formal as described above, wherein the cyclic formal is 1,3-dioxolan.

The above and other objects, features and advantages of the present invention will become apparent from the following description.

DETAILED DESCRIPTION OF THE INVENTION AND PREFERRED EMBODIMENTS

The present invention is directed to a purification process of cyclic formals, and specific examples of the cyclic formals to which the present invention is applicable include 1,3-dioxolan, 1,4-butanediol formal, diethylene glycol formal, 4-methyl-1,3-dioxolan and 1,3-dioxane, with 1,3-dioxolan being preferable.

Figure 1:
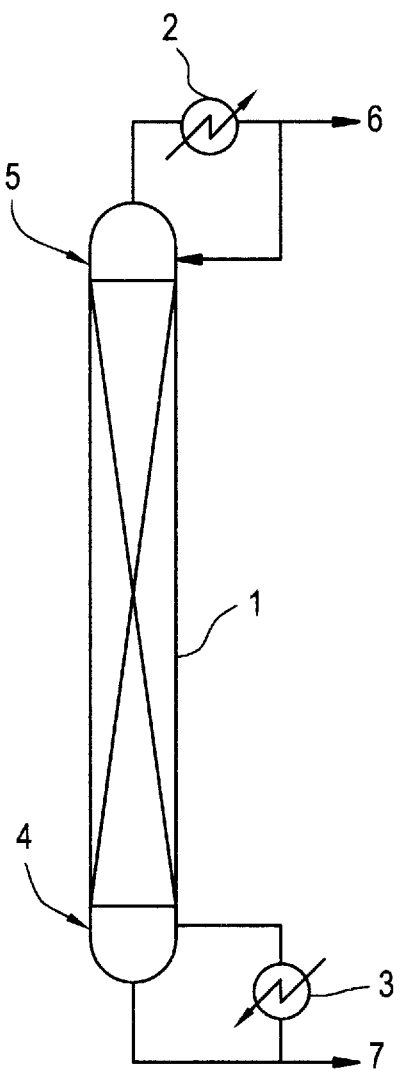
FIG. 1 is a schematic diagram showing a conceptional example of the distillation system used for performing the purification process for cyclic formals according to the present invention.

The present invention will now be described with reference to the distillation system shown in FIG. 1. In FIG. 1, numeral 1 indicates a distillation tower, numeral 2 indicates a condenser, numeral 3 indicates a reboiler, numeral 4 indicates a supply position of a mixture containing a cyclic formal and water, numeral 5 indicates a supply position of a hydrophilic solvent (A), numeral 6 indicates a distillate at the top (may be referred to as a top distillate), and numeral 7 indicates a bottom waste. As described hereinbefore, purification of cyclic formals involves a limitation, that is, they cannot be purified beyond the azeotropic composition of a cyclic formal and water by ordinary distillation procedures. However, according to the present invention, supply of a hydrophilic solvent (A) into the distillation tower destroys the azeotropic system formed in ordinary distillations, allowing water and impurities to be removed and yielding highly purified cyclic formals at the top of the tower. Water contained in the starting mixture, part of a cyclic formal, hydrophilic solvent (A), and impurities such as formaldehyde and reaction biproducts are taken out as a bottom waste from the bottom of the tower.

The hydrophilic solvents (A) used in the present invention are preferably those which are miscible with water in arbitrary proportions at ordinary temperatures, and have a boiling point from 180° to 250° C., preferably from 190° to 250° C. Examples of the hydrophilic solvents (A) include polyols, dimers of polyols and monoalkylethers of polyols and the dimers. Preferable alkyl groups of the monoalkylethers are those having 1 to 4 carbon atoms, among which methyl and ethyl are more preferred, with methyl being particularly preferred. Specific examples of the hydrophilic solvents (A) include 1,4-butanediol, diethylene glycol, 1,2-propanediol, 1,3-propanediol, dipropylene glycol, ethylene glycol and 1,4-butanediol monomethyl ether, diethylene glycol monomethyl ether, 1,2-propanediol monomethyl ether, 1,3-propanediol monomethyl ether, dipropylene glycol monomethyl ether, and ethylene glycol monomethyl ether. These hydrophilic solvents (A) are used singly or in arbitrary combination of two or more. Among the species of hydrophilic solvents (A), 1,4-butanediol, diethylene glycol, 1,2-propanediol are preferred.

The amount of hydrophilic solvent (A) to supply is not particularly limited. It is generally from 1 to 15 times, particularly preferably from 1.5 to 10 times, in a molar ratio, the quantity of water contained in the mixture of cyclic formal and water.

As described above, when cyclic formals are prepared by a conventional process, they contain a considerable amount of water. Taking 1,3-dioxolan as an example of a cyclic formal, reaction between an aqueous solution containing 50% by weight of formaldehyde and an equimolar amount of ethylene glycol to formaldehyde theoretically yields a mixture of 60.7% by weight of 1,3-dioxolan and 39.3% by weight of water. Here, it should be borne in mind that the mixture, which is a starting material of the present invention, desirably contains possibly least impurities. Therefore, in the preparation of a cyclic formal, where a corresponding glycol and formaldehyde in the form of formalin are fed into a reaction vessel for allowing to react each other, it is preferable that the reaction vessel is equipped with a distillation tower thereon so that the mixture to be used is purified by distillation for preventing these starting materials and by-products of the reaction which will act as impurities from migrating into and contaminating the mentioned mixture.

When the above-described cyclic formals containing a considerable amount of water are required to be further purified by extraction distillation, a considerable amount of hydrophilic solvent (A) is needed. To deal with a lot of hydrophilic solvent (A), the diameter of the distillation tower must be increased and the tower itself must be high. This means increased cost of installation which invites increased cost of the purification. Moreover, in cases where the hydrophilic solvent (A) is recovered from the bottom waste for reuse, considerable amounts of water must be removed therefrom, which requires high energy. Accordingly, in the practice of the present invention, it is preferred that the mixture to be supplied be properly dehydrated in advance by ordinary distillation procedures or the like so as to raise the concentration of cyclic formal not less than 80% by weight, preferably in the range from 90% by weight to a concentration of the azeotrope (if the content of the cyclic formal in the azeotropic mixture is not less than 90% by weight).

In the purification process according to the present invention, the position at which the hydrophilic solvent (A) is supplied to the distillation tower is any position higher than the supply position of the mixture of cyclic formal and water. It is preferred that the distance between the two positions be as long as possible. Since the hydrophilic solvents (A) to be used in the present invention have high boiling points, their migration into the target product, purified cyclic formal 6, is a negligibly small amount, which feature is notable in the present invention. However, in order to prevent least hydrophilic solvent (A) from migrating into the top distillate and contaminating it, not a top but a lower supply position may be recommended. For example, when the distillation tower is a plate distillation tower, the supply position is preferably the second from the top (plate No.2) or a lower plate, more preferably between the second (No. 2) to fifteenth (No. 15) plates counted from the top plate. Moreover, in order to enhance the efficiency of water separation and removal, it is preferred that the distance between the supply position of the mixture of a cyclic formal and water and that of the hydrophilic solvent (A) be not less than 10 plates, more preferably, not less than 20 plates. This sufficiently prevents the hydrophilic solvent (A) from migrating into the purified cyclic formal and contaminating it, and also suppresses the water content in the purified cyclic formal 6 at a low level. Similarly, when the distillation tower is a packed distillation tower, the position at which the hydrophilic solvent (A) is supplied is preferably not higher than 0.5 in terms of the theoretical plate number counted from the top of the tower, more preferably between 0.5 to 10 (theoretical plate Nos.). In order to enhance the efficiency of water separation and removal, it is preferred that the distance between the supply position of the mixture of a cyclic formal and water and that of the hydrophilic solvent (A) be not less than 5 plates, more preferably, not less than 10 plates. In this connection, the supply position of the mixture may be at the positions of plates, packed portion, or bottom of the tower as long as the above conditions are met.

No particular limitation is imposed on the types of distillation tower useful for purifying cyclic formals according to the present invention. In cases where plate distillation towers are used, any known types are usable including bubble cap tray, uniflux tray, bulb tray, Natter bulb tray, ballast tray, sieve tray, Venturi tray, Kittel tray, turbo grid tray, ripple tray and the like.

The distillation tower may be a packed distillation tower. Any types of packing materials are usable including those of ring types such as Raschig rings, Lessing rings, divided rings and pole rings; saddle types such as bar saddles and interlock saddles; and other types such as Goodroigh packings, Stedman packings, Dickson rings, McMahon packings, helix packings, teralet, cross-spiral packings and so on.

According to the purification process of the present invention, even when the mixture of cyclic formal and water to be supplied to the distillation tower contain unreacted formaldehyde or reaction byproducts, most of them can be satisfactorily removed. Moreover, although the cyclic formal obtained as a top distillate according to the present invention has been highly purified, it may further be subjected to another distillation or adsorption steps if necessary. The purification process of the present invention is especially useful for purifying 1,3-dioxolan.

EXAMPLES

The present invention will further be described by way of examples, which however, should not be construed as limiting the invention thereto.

Examples 1 to 3

Figure 2:
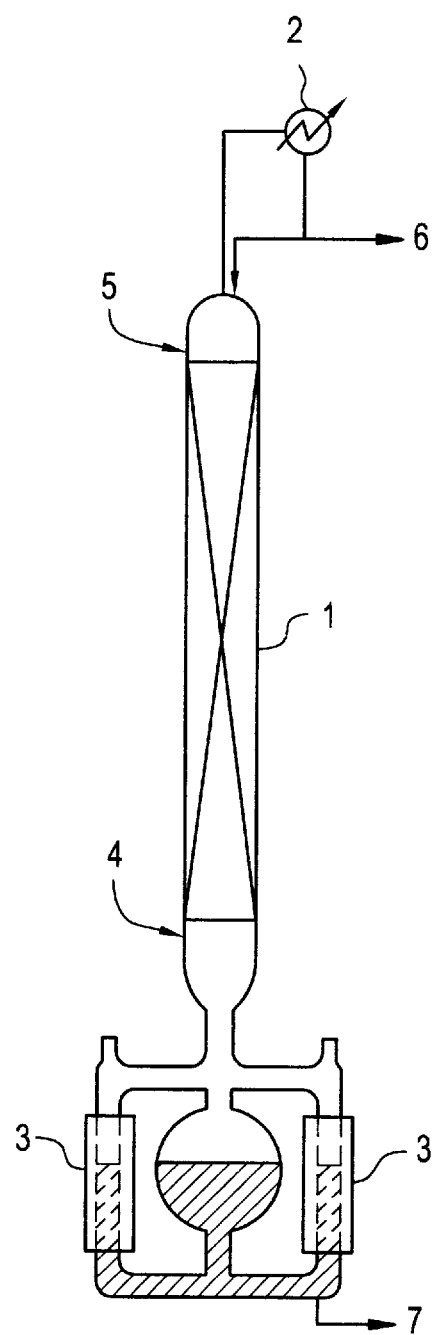
FIG. 2 is a schematic diagram showing the distillation system used in Examples 1 to 13 according to the present invention.

Distillation was performed using a distillation system as shown in FIG. 2, where the distillation tower 1 was a plate distillation tower (diameter of the tower=50 mm, 50 plates, sieve tray). The distillation tower 1 was fed with a mixture containing 93% by weight of 1,3-dioxolan and 7% by weight of water at the bottom of the tower at a flow rate shown in Table 1, while a hydrophilic solvent (A) shown in Table 1 was fed at the top plate at the flow rate shown in Table 1. The flow rates of distillate 6 from the top and waste 7 from the bottom under the steady conditions are shown in Table 1. The compositions of the top distillate and the bottom waste under the steady conditions are shown in Table 2. As apparent from Table 2, a very pure 1,3-dioxolan containing extremely small amounts of water was obtained as a distillate.

The mixture supplied to the tower in this example had a composition close to the azeotrope of 1,3-dioxolan and water, from which ordinary distillation procedures cannot remove water, that is, 1,3-dioxolan can no more be purified by conventional processes.

TABLE 1

|  | Ex. 1 | Ex. 2 | Ex. 3 |
| --- | --- | --- | --- |
| Hydrophilic solvent (A) | BD | DEG | PD |
| Flow rate of mixture supplied (g/hr) | 301 | 389 | 306 |
| Flow rate of hydrophilic solvent (A) supplied (g/hr) | 605 | 699 | 703 |
| Flow rate of distillate from the top (g/hr) | 242 | 322 | 211 |
| Flow rate of waste from the bottom (g/hr) | 664 | 766 | 798 |

BD: 1,4-butanediol
DEG: diethylene glycol
PD: 1,2-propanediol

TABLE 2

|  | Ex. 1 | Ex. 2 | Ex. 3 |
| --- | --- | --- | --- |
|  | Hydrophilic solvent (A): | | |
|  | BD | DEG | PD |
| Distillate from the top | | | |
| 1,3-Dioxolan (% by weight) | 99.9 | 99.9 | 99.9 |
| Water (ppm) | 730 | 615 | 950 |
| Hydrophilic solvent (A) (ppm) | 210 | 200 | 640 |
| Waste from the bottom | | | |
| 1,3-Dioxolan (% by weight) | 5.7 | 5.1 | 9.2 |
| Water (% by weight) | 3.2 | 3.6 | 2.7 |
| Hydrophilic solvent (A) (% by weight) | 91.1 | 91.3 | 88.1 |

BD: 1,4-butanediol
DEG: diethylene glycol
PD: 1,2-propanediol

Examples 4 to 6

The procedure of Examples 1 to 3 was followed except that the supply position of the hydrophilic solvent (A) was changed from the top to the second plate. The flow rates of liquids supplied were carefully controlled so that they became equal to those in Examples 1 to 3, respectively. The compositions of the top distillates and the bottom wastes under the steady conditions are shown in Table 3. As apparent from the Table, 1,3-dioxolan of high purity containing extremely small amounts of water and hydrophilic solvent (A) was obtained as a distillate. The compositions of the bottom wastes were almost the same as those in Examples 1 to 3, respectively.

TABLE 3

|  | Ex. 4 | Ex. 5 | Ex. 6 |
| --- | --- | --- | --- |
|  | Hydrophilic solvent (A): | | |
|  | BD | DEG | PD |
| Distillate from the top | | | |
| 1,3-Dioxolan (% by weight) | 99.9 | 99.9 | 99.9 |
| Water (ppm) | 750 | 640 | 960 |
| Hydrophilic solvent (A) (ppm) | 15 | 20 | 360 |

BD: 1,4-butanediol
DEG: diethylene glycol
PD: 1,2-propanediol

Examples 7 to 9

The procedure of Examples 1 to 3 was followed except that the supply position of hydrophilic solvent (A) was changed from the top to the tenth plate. The flow rates of liquids supplied were carefully controlled so that they became equal to those in Examples 1 to 3, respectively. The compositions of the top distillates and the bottom wastes under the steady conditions are shown in Table 4. As apparent from the Table, 1,3-dioxolan of high purity containing extremely small amounts of water and hydrophilic solvent (A) was obtained as a distillate. The compositions of the bottom wastes were almost the same as those in Examples 1 to 3, respectively.

TABLE 4

|  | Ex. 7 | Ex. 8 | Ex. 9 |
|---|---|---|---|
|  | Hydrophilic solvent (A): | | |
|  | BD | DEG | PD |
| Distillate from the top | | | |
| 1,3-Dioxolan (% by weight) | 99.9 | 99.9 | 99.9 |
| Water (ppm) | 780 | 660 | 1000 |
| Hydrophilic solvent (A) (ppm) | 4 | 6 | 211 |

BD: 1,4-butanediol
DEG: diethylene glycol
PD: 1,2-propanediol

Examples 10 to 11

The procedure of Examples 1 to 3 was followed except that the hydrophilic solvent (A) was changed and the supply position of it was changed from the top to the tenth plate. The flow rates of liquids supplied are shown in Table 5. The compositions of the top distillates and the bottom wastes under the steady conditions are shown in Table 6. As apparent from the Table, 1,3-dioxolan containing less water than contained in azeotrope was obtained as a distillate.

TABLE 5

|  | Ex. 10 | Ex. 11 |
|---|---|---|
| Hydrophilic solvent (A) | DEGMME | DPG |
| Flow rate of mixture supplied (g/hr) | 415 | 402 |
| Flow rate of hydrophilic solvent (A) supplied (g/hr) | 788 | 684 |
| Flow rate of distillate from the top (g/hr) | 262 | 300 |
| Flow rate of waste from the bottom (g/hr) | 941 | 786 |

DEGMME: diethylene glycol monomethylether
DPG: dipropylene glycol

TABLE 6

|  | Ex. 10 | Ex. 11 |
|---|---|---|
|  | Hydrophilic solvent (A): | |
|  | DEGMME | DPG |
| Distillate from the top | | |
| 1,3-Dioxolan (% by weight) | 96.9 | 98.2 |
| Water (% by weight) | 2.99 | 1.77 |
| Hydrophilic solvent (A) (ppm) | 134 | 29 |
| Waste from the bottom | | |
| 1,3-Dioxolan (% by weight) | 12.9 | 9.6 |
| Water (% by weight) | 3.1 | 3.4 |
| Hydrophilic solvent (A) (% by weight) | 84 | 87 |

Examples 12 to 13

Distillation was performed using a distillation system shown in FIG. 2, where the distillation tower 1 was a packed distillation tower (diameter of the tower=50 mm, 22 theoretical plates, packed with metallic Raschig rings). During distillation, the tower was fed with a mixture containing 93% by weight of 1,3-dioxolan and 7% by weight of water at the bottom at a flow rate shown in Table 7, while a hydrophilic solvent (A) was fed at the second theoretical plate from the top at a flow rate shown in Table 7. The flow rates of top distillates and bottom wastes under the steady conditions are shown in Table 7. The compositions of the top distillates and the bottom wastes are shown in Table 8. As apparent from Table 8, a very pure 1,3-dioxolan containing extremely small amounts of water and hydrophilic solvent (A) was obtained as a distillate.

TABLE 7

|  | Ex. 12 | Ex. 13 |
|---|---|---|
| Hydrophilic solvent (A) | BD | DEG |
| Flow rate of mixture supplied (g/hr) | 300 | 350 |
| Flow rate of hydrophilic solvent (A) supplied (g/hr) | 500 | 450 |
| Flow rate of distillate from the top (g/hr) | 210 | 280 |
| Flow rate of waste from the bottom (g/hr) | 590 | 520 |

BD: 1,4-butanediol
DEG: diethylene glycol

TABLE 8

|  | Ex. 12 | Ex. 13 |
|---|---|---|
|  | Hydrophilic solvent (A): | |
|  | BD | DEG |
| Distillate from the top | | |
| 1,3-Dioxolan (% by weight) | 99.9 | 99.9 |
| Water (ppm) | 750 | 720 |
| Hydrophilic solvent (A) (ppm) | 15 | 20 |
| Waste from the bottom | | |
| 1,3-Dioxolan (% by weight) | 11.8 | 8.8 |
| Water (% by weight) | 3.5 | 4.7 |
| Hydrophilic solvent (A) (% by weight) | 84.7 | 86.5 |

BD: 1,4-butanediol
DEG: diethylene glycol

Examples 14 to 16

Distillation was performed using a distillation system as shown in FIG. 2, where the distillation tower 1 was a plate distillation tower (diameter of the tower=50 mm, 50 plates, sieve tray). The distillation tower 1 was fed with a mixture containing 60.5% by weight of 1,3-dioxolan and 39.5% by weight of water at the bottom of the tower 1 at a flow rate shown in Table 9, while a hydrophilic solvent (A) shown in Table 9 was fed at the top plate at the flow rate shown in Table 9. The flow rates of distillate 6 from the top and waste 7 from the bottom under the steady conditions are shown in Table 9. The compositions of the top distillate and the bottom waste under the steady conditions are shown in Table 10. As apparent from Table 10, 1,3-dioxolan of high concentration which exceeds the %1,3-dioxolan of the azeotropic composition was obtained as a distillate.

TABLE 9

|  | Ex. 14 | Ex. 15 | Ex. 16 |
|---|---|---|---|
| Hydrophilic solvent (A) | BD | DEG | PD |
| Flow rate of mixture supplied (g/hr) | 252 | 258 | 247 |
| Flow rate of hydrophilic solvent (A) supplied (g/hr) | 650 | 750 | 800 |
| Flow rate of distillate from the top (g/hr) | 108 | 115 | 105 |

TABLE 9-continued

|  | Ex. 14 | Ex. 15 | Ex. 16 |
|---|---|---|---|
| Flow rate of waste from the bottom (g/hr) | 794 | 893 | 942 |

BD: 1,4-butanediol
DEG: diethylene glycol
PD: 1,2-propanediol

TABLE 10

|  | Ex. 14 | Ex. 15 | Ex. 16 |
|---|---|---|---|
|  | Hydrophilic solvent (A): | | |
|  | BD | DEG | PD |
| Distillate from the top | | | |
| 1,3-Dioxolan (% by weight) | 99.6 | 99.7 | 99.5 |
| Water (ppm) | 3500 | 3200 | 4500 |
| Hydrophilic solvent (A) (ppm) | 225 | 210 | 620 |
| Waste from the bottom | | | |
| 1,3-Dioxolan (% by weight) | 5.6 | 4.6 | 4.7 |
| Water (% by weight) | 12.3 | 11.2 | 10.3 |
| Hydrophilic solvent (A) (% by weight) | 82.1 | 84.2 | 85.0 |

BD: 1,4-butanediol
DEG: diethylene glycol
PD: 1,2-propanediol

As described hereinabove, the present invention provides an economical purification process for crude cyclic formals containing water which was conventionally thought to be difficult to purify because of the azeotropy between the formals and water. The process of the invention yields highly pure cyclic formals on a steady basis, and is very useful and advantageous in the industry.

I claim:

1. A purification process for a cyclic formal which comprises the steps of supplying a mixture of a cyclic formal selected from the group consisting of 1,3-dioxolan, 1,4-butanediol formal, diethylene glycol formal, 4-methyl-1,3-dioxolan, 1,3-dioxane and 1,3,6-trioxolane, wherein a pre-concentrated mixture which contains a cyclic formal having a concentration of more than 80% by weight in the mixture up to a concentration which forms an azeotrope, and water into a distillation tower containing 50 plates at a supply position; effecting distillation while supplying a hydrophilic solvent (A) selected from the group consisting of 1,4-butanediol monomethyl ether, diethylene glycol monomethyl ether, 1,2-propanediol monomethyl ether, 1,3-propanediol monomethyl ether, dipropylene glycol monomethyl ether, and ethylene glycol monomethyl ether having a boiling point from 180° to 250° C. at a position higher than the supply position of the mixture; and taking out a purified cyclic formal as a distillate and the hydrophilic solvent containing water as a bottom waste.

2. The process according to claim 1, wherein the quantity of the hydrophilic solvent (A) supplied is from 1 to 15 times, on a molar basis, the quantity of water in the mixture of cyclic formal and water.

3. The process according to claim 1, wherein the distillation tower is a plate distillation tower, and the position at which the hydrophilic solvent (A) is supplied is a position not higher than the second plate counted from the top plate.

4. The process according to claim 1, wherein the distillation tower is a packed distillation tower, and the position at which the hydrophilic solvent (A) is supplied is the position of a theoretical plate having a number not less than 0.5 counted from the top plate of the packed distillation tower.

5. The process according to claim 1, wherein the cyclic formal is 1,3-dioxolan.

6. A purification process for cyclic formals, comprising the steps of supplying a mixture of the cyclic formal and water into a distillation tower containing 50 plates at a supply position, wherein the cyclic formal is 1,3-dioxolan and is characterized by a pre-concentrated mixture which contains a cyclic formal having a concentration of more than 80 weight percent in the mixture up to a concentration which forms an azeotrope; effecting distillation while supplying a hydrophilic solvent selected form the group consisting of 1,4-butanediol monomethyl ether, diethylene glycol monomethyl ether and 1,2-propanediol monomethyl ether at a position in the tower higher than the supply position of the mixture, wherein the solvent is characterized as exhibiting a boiling point from 180° to 250° C.; and taking out a purified cyclic formal as a distillate and hydrophilic solvent containing water as a bottom waste.

7. The process according to claim 6, wherein the quantity of the hydrophilic solvent (A) supplied is from 1 to 15 times, on a molar basis, the quantity of water in the mixture of cyclic formal and water.

8. The process according to claim 6, wherein the distillation tower is a plate distillation tower, and the position at which the hydrophilic solvent (A) is supplied is a position not higher than the second plate counted from the top plate.

9. The process according to claim 6, wherein the distillation tower is a packed distillation tower, and the position at which the hydrophilic solvent (A) is supplied is the position of a theoretical plate having a number not less than 0.5 counted from the top plate of the packed distillation tower.

10. The process according to claim 6 wherein the cyclic formal is 1,3-dioxolan.

* * * * *